United States Patent [19]

Errico et al.

[11] Patent Number: 5,586,984

[45] Date of Patent: *Dec. 24, 1996

[54] POLYAXIAL LOCKING SCREW AND COUPLING ELEMENT ASSEMBLY FOR USE WITH ROD FIXATION APPARATUS

[75] Inventors: Joseph P. Errico, Hempstead, N.Y.; Thomas J. Errico, Summit; James D. Ralph, Oakland, both of N.J.

[73] Assignee: Fastenetix, L.L.C., Summit, N.J.

[ * ] Notice: The term of this patent shall not extend beyond the expiration date of Pat. No. 5,549,608.

[21] Appl. No.: 502,803

[22] Filed: Jul. 14, 1995

Related U.S. Application Data

[63] Continuation-in-part of Ser. No. 502,285, Jul. 13, 1995.

[51] Int. Cl.$^6$ .................................................. A61B 17/70
[52] U.S. Cl. .................................................. 606/61; 606/73
[58] Field of Search ................................. 606/61, 69, 70, 606/71, 72, 73, 66, 65, 60, 59, 54, 104

[56] References Cited

U.S. PATENT DOCUMENTS

| | | | |
|---|---|---|---|
| 4,805,602 | 2/1989 | Puno et al. | 128/69 |
| 4,946,458 | 8/1990 | Harms et al. | 606/61 |
| 4,987,892 | 1/1991 | Krag et al. | 606/61 |
| 5,153,103 | 9/1992 | Tepic et al. | 606/69 |
| 5,176,680 | 1/1993 | Vignaud et al. | 606/61 |
| 5,190,543 | 3/1993 | Schläpfer | 606/61 |
| 5,207,678 | 5/1993 | Harms et al. | 606/61 |
| 5,217,497 | 6/1993 | Mehdian | 623/17 |
| 5,261,909 | 11/1993 | Sutterlin et al. | 606/61 |
| 5,261,912 | 11/1993 | Frig | 606/61 |
| 5,306,275 | 4/1994 | Bryan | 606/61 |
| 5,360,431 | 11/1994 | Puno et al. | 606/72 |
| 5,443,467 | 8/1995 | Biedermann et al. | 606/65 |
| 5,480,401 | 1/1996 | Navas | 606/61 |

*Primary Examiner*—Guy V. Tucker
*Attorney, Agent, or Firm*—Joseph P. Errico

[57] ABSTRACT

A polyaxial orthopedic device for use with rod implant apparatus includes a screw having a curvate head and a coupling element. The coupling element has a tapered lower portion including a slotted interior chamber in which the curvate head is initially polyaxially disposed. The coupling element further includes a recess for receiving the rod of the implant apparatus, and an exterior threading disposed on its upper portion which receives a locking nut. A locking ring is disposed about the lower portion of the coupling element, and provides an inward force on the outwardly tapered portion upon downward translation thereof, thereby causing the vertical slots to close, and crush locking the screw head within the interior chamber, thus eliminating the polyaxial nature of the screw-element coupling. In several embodiments a hollow cylindrical rod securing sleeve is provided which fits over the coupling element and locks the rod to the coupling element. In the other embodiments, the locking nut seats against the top of the rod, locking it in place.

28 Claims, 11 Drawing Sheets

POLYAXIAL LOCKING SCREW AND COUPLING ELEMENT ASSEMBLY FOR USE WITH ROD FIXATION APPARATUS

CROSS-REFERENCE TO PRIOR APPLICATION

This application is a continuation-in-part of prior application U.S. Ser. No. 08/502,285, now pending, entitled "An Advanced Polyaxial Locking Screw And Coupling Element For Use With Rod Fixation Apparatus", filed Jul. 13, 1995.

BACKGROUND OF THE INVENTION

1. Field of the Invention

This invention relates generally to a polyaxial screw and coupling apparatus for use with orthopedic fixation systems. More particularly, the present invention relates to a screw for insertion into spinal bone, and a coupling element polyaxially mounted thereto for coupling the screw to an orthopedic implantation structure, such as a rod, therein enhancing the efficacy of the implant assembly by providing freedom of angulation among the rod, screw and coupling element.

2. Description of the Prior Art

The spinal column is highly complex system of bones and connective tissues which houses and protects critical elements of the nervous system and the arterial and veinous bodies in close proximity thereto. In spite of these complexities, the spine is a highly flexible structure, capable of a high degree of curvature and twist through a wide range of motion.

Genetic or developmental irregularities, trauma, chronic stress, tumors, and disease, however, can result in spinal pathologies which either limit this range of motion, or which threaten the critical elements of the nervous system housed within the spinal column. A variety of systems have been disclosed in the art which achieve this immobilization by implanting artificial assemblies in or on the spinal column. These assemblies may be classified as anterior, posterior, or lateral implants. As the classification suggests, lateral and anterior assemblies are coupled to the anterior portion of the spine, which is the sequence of vertebral bodies. Posterior implants are attached to the back of the spinal column, generally hooking under the lamina and entering into the central canal, attaching to the transverse process, or coupling through the pedicle bone. The present invention relates to spinal fixation devices for immobilizing and altering the alignment of the spine over a large number, for example more than three or four, vertebra by means of affixing at least one elongate rod to the sequence of selected bones.

Such "rod assemblies" generally comprise a plurality of screws which are implanted through the posterior lateral surfaces of the laminae, through the pedicles, and into their respective vertebral bodies. The screws are provided with coupling elements, for receiving an elongate rod therethrough. The rod extends along the axis of the spine, coupling to the plurality of screws via their coupling elements. The aligning influence of the rod forces the spine to which it is affixed, to conform to a more proper shape.

It has been identified, however, that a considerable difficulty is associated with inserting screws along a misaligned curvature and simultaneously exactly positioning the coupling elements such that the receiving loci thereof are aligned so that the rod can be passed therethrough without distorting the screws. Attempts at achieving proper alignment with fixed screws is understood to require considerably longer operating time, which is known to increase the incidence of complications associated with surgery. Often such alignments, with such fixed axes devices could not be achieved, and the entire instrumentationing effort would end unsuccessfully.

In addition, for many patients specific pathology it is desirable that the rod extend down into and beyond the lumbar portion of the spine, and for the end of the rod to be coupled to the sacral bone. Providing such an end to the assembly in the sacral bone has been understandably suggested inasmuch as it provides superior support to the full extent of the assembly. The most suitable position for the insertion of the screws into the sacral body may not, however, conform to the direction extent of the rod as it is affixed to the entirety of the assembly. Misalignment of the rod with respect to the screw and the coupling element is often a source of considerable disadvantage for the surgeon, often requiring considerable efforts to be expended bending and aligning the rod with the receiving locus of the coupling element. These additional efforts are a considerable difficulty associated with the proper and expeditious affixation, and over the long term, the offset of the rod can have a deleterious effect on the overall performance of the entire implantation assembly.

The art contains a variety of attempts at providing instrumentation which permit a freedom with respect to angulation of the screw and the coupling element. These teachings, however, have generally been complex, and inadequately reliable with respect to durability. The considerable drawbacks associated with the prior art systems include complexity, difficulty properly positioned the rod and coupling elements, and the tedious manipulation of the many parts associated with the complex devices.

It is, therefore, the principal object of the present invention to provide a pedicle screw and coupling element assembly which provides a polyaxial freedom of implantation angulation with respect to rod reception.

In addition, it is an object of the present invention to provide such an assembly which comprises a reduced number of elements, and which correspondingly provides for expeditious implantation.

Accordingly it is also an object of the present invention to provide an assembly which is reliable, durable, and provides long term fixation support.

Other objects of the present invention not explicitly stated will be set forth and will be more clearly understood in conjunction with the descriptions of the preferred embodiments disclosed hereafter.

SUMMARY OF THE INVENTION

The preceding objects of the invention are achieved by the present invention which is a polyaxial locking screw and coupling element for use with rod stabilization and immobilization systems in the spine. More particularly, the polyaxial screw and coupling element assembly of the present invention comprise a bone screw having a head which is curvate in shape, for example semi-spherical, and a coupling element mounted thereon so as to be free to rotate and angulate prior to the secure fixation of the rod thereto, and which may be securely locked in a given angulation once the rod is received by the coupling element. In its various embodiments, the coupling element generally comprises a cylindrical main body portion, a locking collar, a removeable external rod securing sleeve, and a top locking nut. In at least one embodiment, however, the removeable external rod securing sleeve is not required.

The coupling element may be conceptually divided into a lower socket portion, and a top rod receiving portion. The lower socket portion includes an interior chamber having an opening at the bottom thereof. The interior chamber is ideally suited for receiving therein the head of the screw such that the screw and the coupling element are held together in a rotationally free relationship. The external surface of the socket portion includes at least one vertical slot which is provided so that the opening in the bottom of the element may expand to receive the head of the screw, which has a major diameter which is larger than the unexpanded opening, such that the head of the screw may enter into the interior chamber. The at least one slot resiliently expands to permit the head of the screw to enter, and subsequently contracts into its original position once the head is fully inserted, therein inhibiting the screw head from being retracted. The head of the screw and the interior chamber are, however, free to rotate relative to one another.

The exterior of the lower portion of the coupling element, into which the screw head is inserted, tapers outward slightly toward the bottom of the element, therein having a slightly wider diameter at the bottom than at the top thereof. A locking ring, having a diameter equal to, or greater than the top of the lower portion, but less than the diameter of the bottom of the lower portion, is initially disposed about the top of the lower portion. Translation downward by the locking ring causes the at least one vertical slot in the lower portion of the coupling element to close, therein causing the inner surface of the interior chamber to move radially inward, contacting the head of the screw, and crush locking thereto.

The top rod receiving portion of the coupling element comprises a central channel formed vertically downward into the body of the coupling element. More particularly, from a position above the lower portion, a section of the generally cylindrical body which extends upward therefrom is removed therein providing a receiving locus into which a support rod may nest. The top portion of the coupling element, therefore, comprises a U-shape, the inner surfaces of the top portion being spaced apart sufficiently to receive the support rod therein.

In a first embodiment, in order that the rod may be securely held within the receiving locus, an external rod securing sleeve is provided. The external rod securing sleeve is generally cylindrical in shape, having a hollow center for sliding over the top of the coupling element. The opposing sides of the rod securing sleeve include vertically aligned rounded slots, dividing the bottom portion of the sleeve into two downwardly extending members and therein providing the sleeve with a conformation which resembles an upside down u-shape. The bottom edge of the rod securing sleeve comprises a inward beveling for being received by the upper surface of a locking ring as discussed in more detail hereinafter.

The exterior surface of the uppermost section of the top rod receiving portion of the coupling element comprises a threading onto which a locking nut may be inserted, therein locking the rod securing sleeve onto the coupling element. The bottom surface of the nut is designed to mate with the top edge of the rod securing element. It is the engagement of the nut with the upper portion of the coupling element, and the driving of the nut downward onto the upper portion of the coupling element which causes the rod securing sleeve to be driven downward into its full rod locking position. The rod is, therefore, locked between the curvate bottom of the U-shaped rod receiving locus, and the curvate top of the U-shaped rod securing sleeve.

In this first embodiment, the inner wall of the locking ring and the outer surface of the lower portion of the coupling element are smooth. As stated above, the bottom edge of the rod securing sleeve is designed to mate with the upper surface of the locking sleeve. When the nut driven downward, therein driving the rod securing sleeve downward as well, the sleeve forces the locking ring downward to lock the screw within the interior chamber while simultaneously locking the rod and the rod securing sleeve.

In a second embodiment, in which there is no need for a rod securing sleeve, the top of the locking ring extends further up the body of the coupling element, the top edge thereof being initially disposed at a position above the curvate bottom of the U-shaped rod receiving locus. The locking ring further includes two opposing grooves, or notches, onto which the rod is initially placed. As in the first embodiment, translation of the locking ring downward causes the at least one vertical slot in the lower portion of the coupling element to close, therein causing the screw to be crush locked within the interior chamber. In this embodiment, however, it is not the bottom surface of a rod securing sleeve which applies the translational forces on the locking ring, but rather the rod itself which forces the locking ring downward. The rod is forced downward by the locking nut as it is threaded down onto from above the rod, on the exterior threading of the top portion of the coupling element.

In a third embodiment, which again comprises a rod securing sleeve, the inner wall of the locking ring and the outer surface of the lower portion of the coupling element comprise mateable threadings, oriented such that proper rotation of the ring relative to the coupling element causes the ring to translate down the lower portion toward the bottom of the element. In this embodiment, therefore, the locking ring may be independently driven downward along the lower portion of the coupling element to lock the screw to the coupling element.

In this embodiment, the downward movement of the rod securing sleeve does not force the locking ring into its securing position. However, the bottom of the rod securing sleeve, once in place may, however, interface with the top of the locking ring in order to prevent the locking ring from counter-rotating after implantation, therein unlocking the angulation of the lower portion of the coupling element and the screw head.

In each embodiment, the coupling element includes an axially aligned central bore which extends from the curvate bottom of the rod receiving locus into the interior chamber. The screw head correspondingly includes a recess, which is alignable with the central bore of the coupling element, whereby a screw-driving instrument may be inserted through the central bore, into the recess in the screw, and utilized to drive the screw into the bone.

The first step in the process of implanting any of the embodiments of the invention is to insert the head of the screw into the interior chamber of the coupling element. Once it has been inserted, the angle of insertion at which the screw will have the greatest holding strength relative to the loading which the rod system will be applying thereto must be determined. Once this angle has been found, a drill may be employed to form an insertion hole into which the screw may be inserted. The screw and the coupling element are correspondingly aligned with respect to one another so that a screw-driving tool may be inserted down the central bore of the coupling element, into the recess in the head of the screw, and thereby be rotationally inserted into the bone. Subsequent to the insertion of the screw, the screw-driving device is removed from the assembly, therein permitting the coupling element to rotate and change angular alignment relative to the screw.

In the second embodiment, in which the locking ring and the lower portion of the coupling element are threaded, the coupling element is positioned in anticipation of receiving the rod, and then the locking ring is rotated into a locking position thereby securing the relative angle of the screw and the coupling element. In the first and third embodiments, the locking of the screw to the coupling element by the downward translation of the locking ring is necessarily delayed until the rod has been inserted into the rod receiving locus.

In the first and third embodiments, as the rod of the implantation apparatus is then provided into the receiving locus, the coupling element is moved relative to the screw so that the position of rod within the coupling element may be optimized.

In the first and second embodiments, once the rod has been properly positioned, the securing sleeve is placed onto the coupling element, with the rod extending through the opposing vertical slots thereof.

In the third embodiment, the rod is simply nested on the grooves of the locking ring in anticipation of the downward force of the top locking nut.

In all three embodiments the locking nut is then introduced onto the top of the coupling element.

It is understood that the use of a particular embodiment shall be at the discretion of the surgeon, in accordance with the determination of the proper protocol for use with respect to each patient. In addition, it shall be understood that the curvate shape of the head of the screw may be chosen from the various specific shapes which are compatible with the general polyaxial concept of the present invention. For the purposes of providing specific variations of the embodiments described above, and set forth more fully hereinbelow with respect to the drawings, two possible shapes of the screw head are provided, the first being fully semi-spherical and the second being hemispherical (having a flattened top profile. The choice of using flattened top profile versus a fully semi-spherical profile is associated with the height of the overall screw and coupling element, the semi-spherical (or ball) head of the screw providing for a higher seating of the coupling element versus the hemispherical flattened head.

Multiple screw and coupling element assemblies are generally necessary to complete the full array of anchoring sites for the rod immobilization system, however, the screw and coupling element assembly of the present invention are designed to be compatible with alternative rod systems so that, where necessary, the present invention may be employed to rectify the failures of other systems the implantation of which may have already begun.

DETAILED DESCRIPTION OF THE PREFERRED EMBODIMENT

While the present invention will be described more fully hereinafter with reference to the accompanying drawings, in which particular embodiments and methods of implantation are shown, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope.

Figure 1:
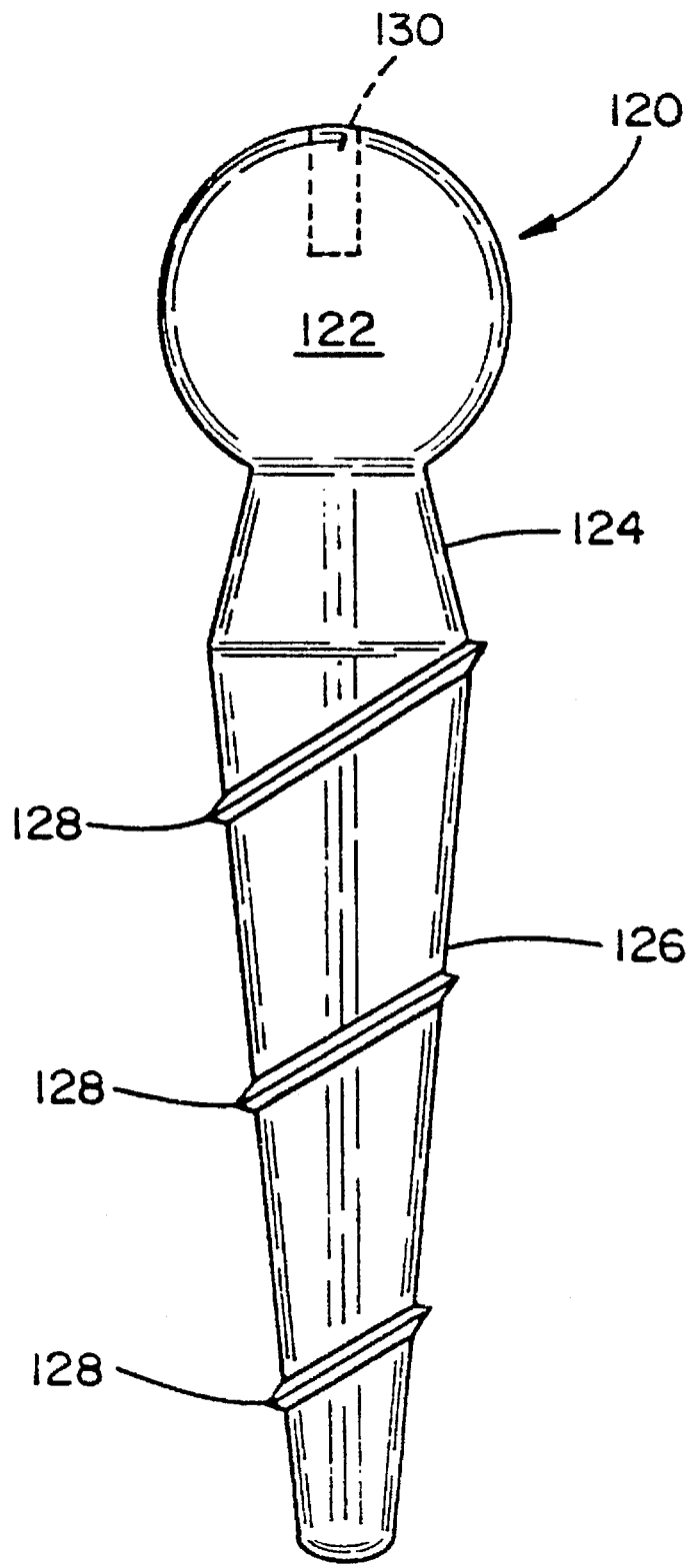
FIG. 1 is a side view of a screw having a curvate head which is an aspect of the present invention.
Figure 5:
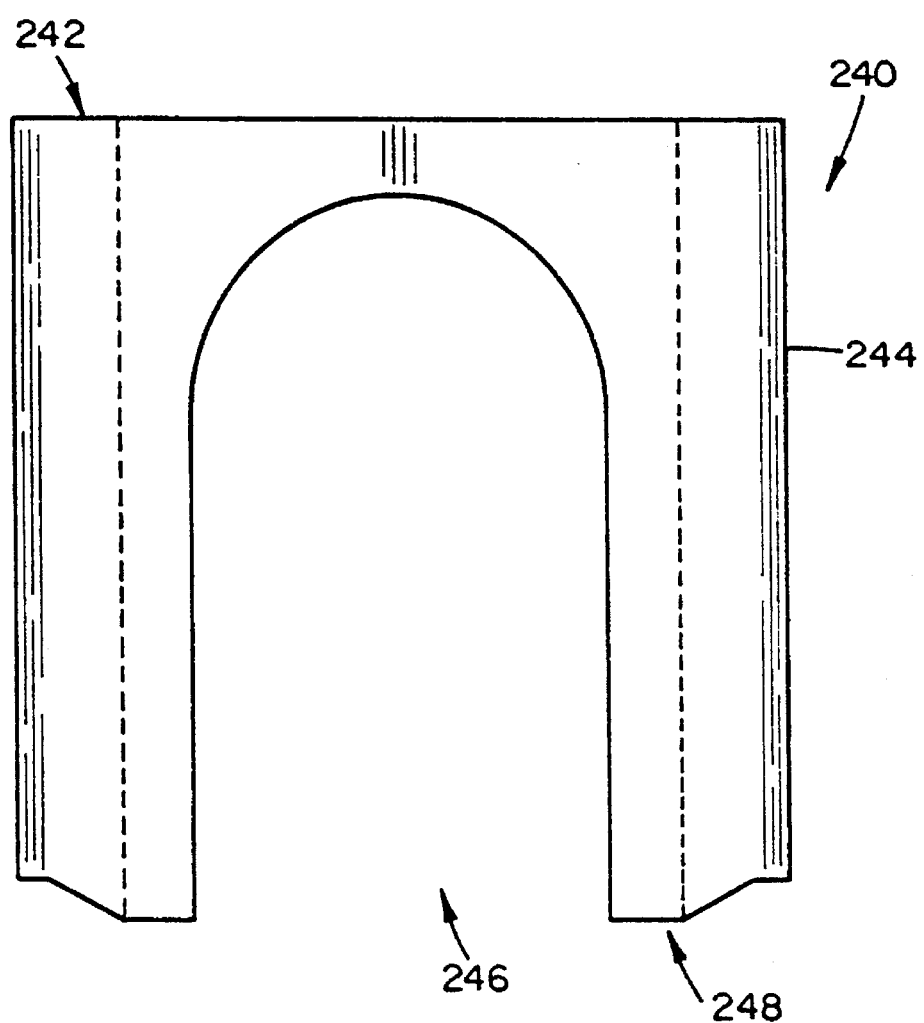
FIG. 5 is a side cross-sectional view of the rod securing sleeve of the first embodiment, shown along a direction wherein the vertical slots therein are aligned perpendicular to the plane of view.

Referring now to FIG. 1, a side view of the screw portion of the present invention, comprising a curvate head, is shown. The screw 120 comprises a head portion 122, a neck 124, and a shaft 126. In FIG. 5, the shaft 126 is shown as having a tapered shape with a high pitch thread 128. It shall be understood that a variety of shaft designs are interchangeable with the present design. The specific choice of shaft features, such as thread pitch, shaft diameter to thread diameter ratio, and overall shaft shape, should be made be the physician with respect to the conditions of the individual patient's bone, however, this invention is compatible with a wide variety of shaft designs.

The head portion 122 of the screw 120 comprises a semi-spherical shape, which has a recess 130 in it. It is understood that the semi-spherical shape is a section of a sphere, in the embodiment shown the section is greater in extent than a hemisphere, and it correspondingly exhibits an external contour which is equidistant from a center point of the head. In a preferred embodiment, the major cross-section of the semi-spherical head 122 (as shown in the two dimensional illustration of FIG. 5) includes at least 270 degrees of a circle.

The recess 130 defines a receiving locus for the application of a torque for driving the screw 120 into the bone. The specific shape of the recess 122 may be chosen to cooperate with any suitable screw-driving tool. For example, the recess 130 may comprise a slot for a flat-headed screwdriver, a crossed recess for a phillips head screwdriver, or most preferably, a hexagonally shaped hole for receiving an allen wrench. It is further preferable that the recess 130 be co-axial with the general elongate axis of the screw 120, and most particularly with respect to the shaft 126. Having the axes of the recess 130 and the shaft 126 co-linear facilitates step of inserting the screw 120 into the bone.

The semi-spherical head portion 122 is connected to the shaft 126 at a neck portion 124. While it is preferable that the diameter of the shaft 126 be less than the diameter of the semi-spherical head 122, it is also preferable that the neck 124 of the screw 120 be narrower than the widest portion of the shaft 126. This preferable dimension permits the screw to be locked at a variety of angles while still being securely joined to the coupling element (embodiments of which are shown in the remaining Figures).

Figure 2:
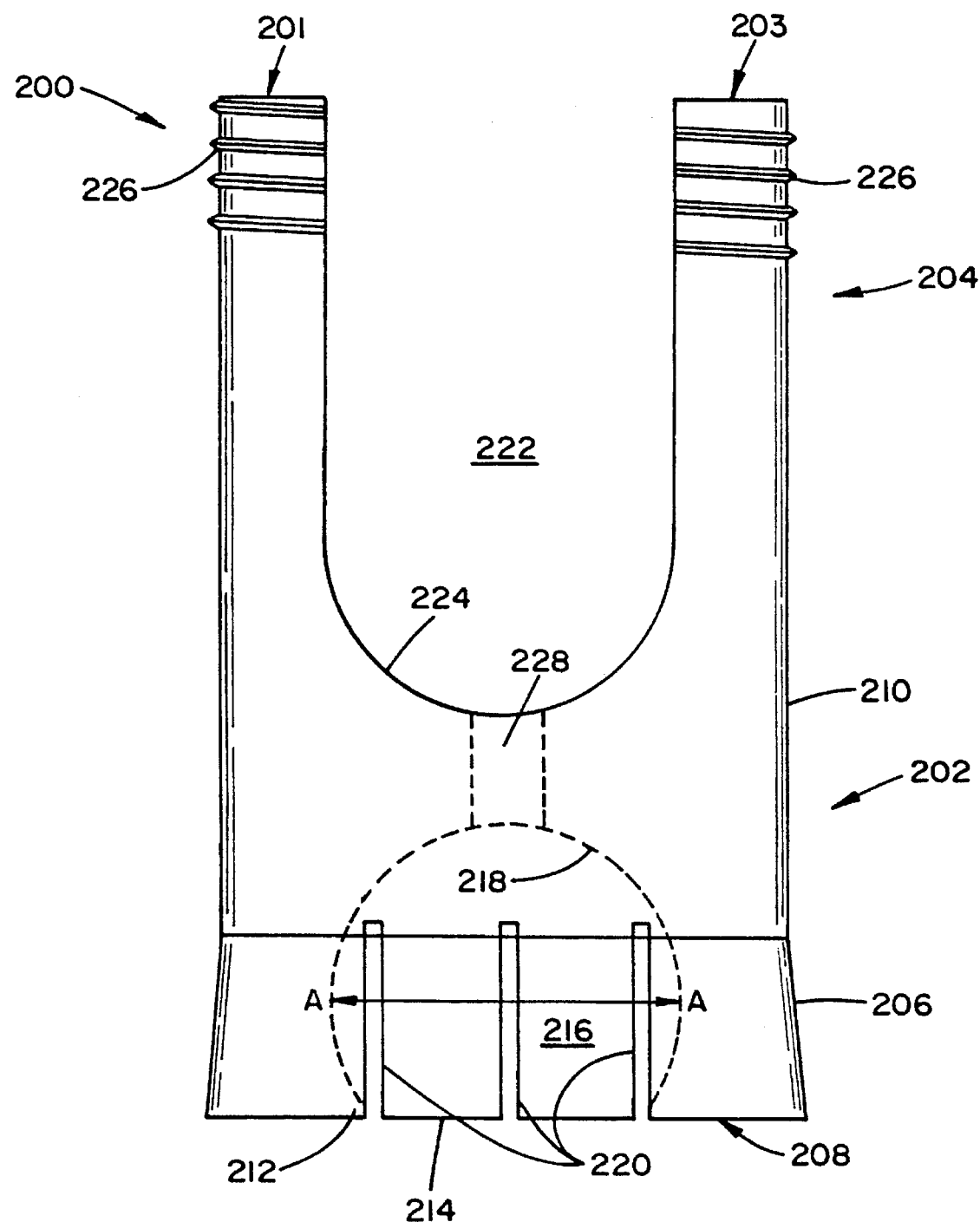
FIG. 2 is a side view of the coupling element of a first embodiment of the present invention.

Referring now to FIG. 2, a first embodiment of the coupling element 200 of the present invention is shown in a side view, wherein several critical features of the interior of the element are shown in phantom. The coupling element 200 comprises a generally cylindrical body which may be conceptually separated into upper and lower portions 202, 204, respectively, each of which shall be described more fully hereinbelow.

First, with respect to the lower portion 202, the exterior surface 206 of the body is tapered in the elongate direction such that the body is wider at the bottom 208 of the lower portion 202 than at the top 210 thereof. The bottom 208 of the element includes an opening 214, defined by annular lip 212, which forms the mouth of an interior chamber 216. The diameter of the opening 214, when otherwise unaffected by external deflecting forces, is more narrow than the maximum diameter A—A of the interior chamber 216. The interior chamber 216 has a generally curvate inner surface 218 which is correspondingly shaped to receive the semi-spherical head 122 of the screw 120.

The exterior surface 206 of the lower portion 202 includes a series of slots 220 which extend vertically upward from the bottom 208 of the element to a point which is closer to the top 210 of the lower portion 202 than the maximum horizontal diameter A—A. The slots 220 are provided in order that the application of an external deflecting force may widen or narrow the opening 214 therein permitting the insertion of an object which is larger than the undeflected diameter of the opening 214, or conversely, providing for the retention of an object which is smaller than the undeflected diameter of the opening 214.

The upper portion 204 of the generally cylindrical body of the coupling element 200 includes a large removed section which forms a vertically oriented channel, therein forming a rod receiving locus 222 in the top of the coupling element 200. The rod receiving locus 222 comprises a curvate bottom surface 224 which, for example defines a semi-circular cross-section. The depth of the channel 224 is such that a circular support rod (see FIG. 6) which is positioned in the rod receiving locus 222 may nests fully within the coupling element 200, the top of the rod thereby being positioned substantially below the top of the upper portion. This permits the rod securing sleeve (such as shall be described with reference to FIG. 5) to slide over top of the coupling element 200 to retain the rod within the rod receiving locus 222, and further permits the top locking nut (see FIG. 4) to be disposed on the top of the coupling element in a manner described more fully hereinbelow.

The upper portion 204 of the coupling element 200, which comprises a pair of spaced apart upwardly extending members 201, 203, comprises an external surface threading 226. These members 201, 203, and the threading 226 thereon, are ideally suited for receiving a top locking nut (see FIG. 6).

A central bore 228 extends axially from the currate bottom surface 224 of the rod receiving locus 222 into the interior chamber 216 of the lower portion 202. The bore 228, therefore, provides a linear passage through which a user may insert a screw-driving tool to access the interior chamber 216, and the recess of the screw 120 which may be positioned therein.

Figure 3:
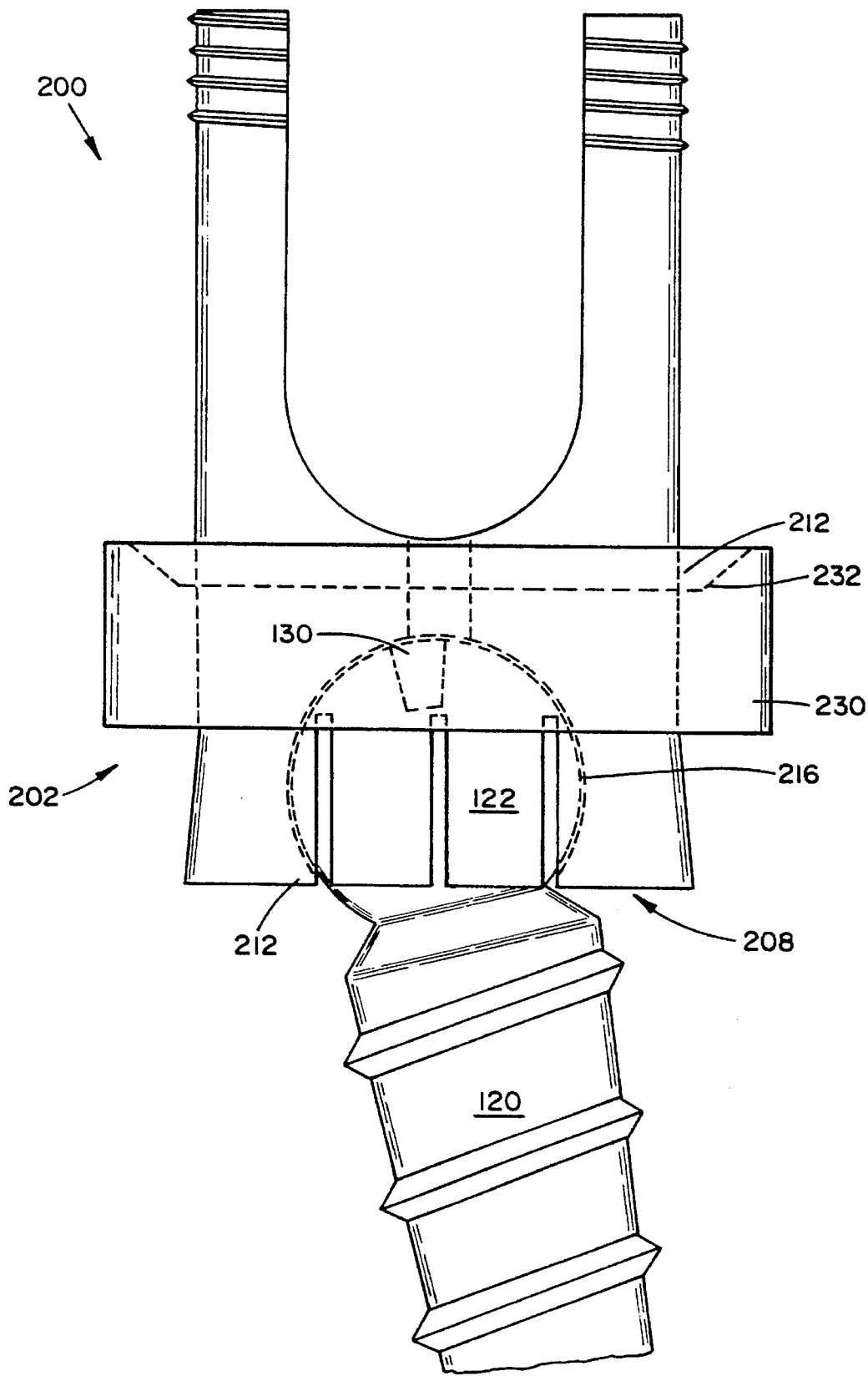
FIG. 3 is a side view of the coupling element shown in FIG. 2, having the screw shown in FIG. 1 inserted into the interior chamber therein, and including a locking ring in an unsecured position.
Figure 6:
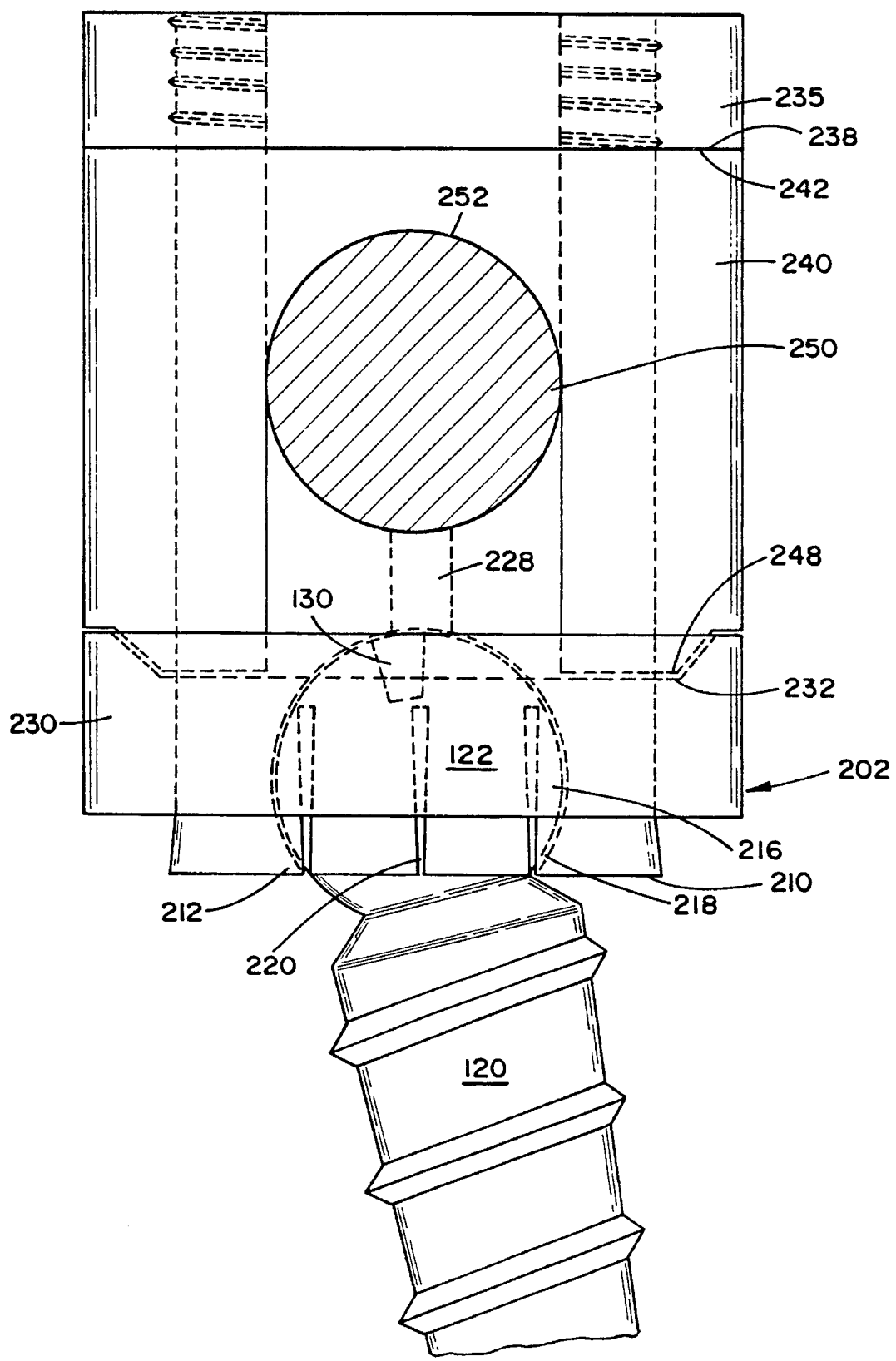
FIG. 6 is a side cross-sectional view of the first embodiment of the present invention in its fully assembled disposition having a rod securely locked therein.

Referring now to FIG. 3, the coupling element 200, as described more fully with respect to FIG. 6, is shown in a side view, wherein the head 122 of the screw 120 has been received within the interior chamber 216, and a locking ring 230 is shown in its pre-locked position about the top 212 of the lower portion 202. The head 122 of the screw 120 is rotationally free to move relative to the coupling element, however, it is prevented from fully separating from the coupling element and the interior chamber 216 by the annular lip 212 at the bottom 208 of the lower portion 202. The locking ring 230 comprises a contiguous annular element having an inner diameter which is equal to the outer diameter of the lower portion 202 at the top 212 thereof. In order to lock the screw 120 into an angle relative to the coupling element 200, therein eliminating the freedom of the screw 120 to swing relative to the coupling element 200, the locking ring must be forced downward relative to the coupling element 200. A dowel, protuberance, or other suitable means may be provided at or above the top 212 of the lower portion 202 so that the ring 230 may not be easily moved upward, and thereby preventing separation of the locking ring during handling prior to use. The top surface 232 of the locking ring 230 is contoured to mate easily with the bottom of the rod securing sleeve (see FIG. 5).

Figure 4:
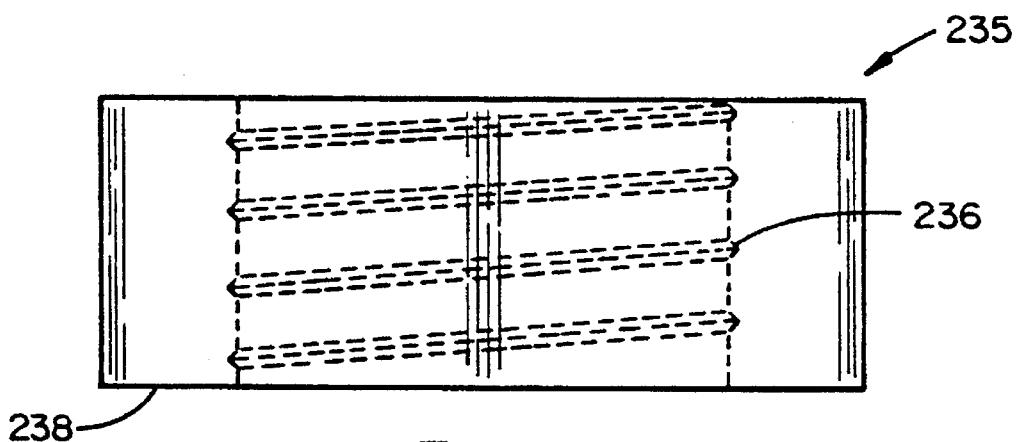
FIG. 4 is a side cross-sectional view of the top locking nut of the present invention.

Referring now to FIGS. 4 and 5, a top locking nut 235 and the rod securing sleeve 240 of the first embodiment are shown in side cross-section views. Referring specifically to FIG. 5, the rod securing sleeve 240 comprises a hollow cylindrical body 244 having diametrically opposing vertical slots 246, which together define a passage through the sleeve for the positioning of a rod therethrough. The opposing vertical slots 246 provide the sleeve 240 with a upsidedown U-shaped cross-section, as illustrated in FIG. 5. The interior diameter (not seen in the side view) of the sleeve 240 is equal to the outer diameter of the coupling element, so that it may be placed over the coupling element. The vertical slots 246 correspond to the channel or rod receiving locus 222 of the upper portion 204 of the coupling element 200, such that the support rod which is inserted therein (see FIG. 6) may pass therethrough. The bottom edge 248 of the rod receiving sleeve 240 is contoured to fit securely with the contour of the upper surface 232 of the locking ring 230.

Referring now also to FIG. 4, the nut 235 comprises an inner threading 236 which is intended to mate with the threading 226 on the upper portion 204 of the coupling element 200. The bottom surface 238 of the nut 235 is intended to seat against the top surface 242 of the rod securing sleeve 240, but is permitted to rotate relative to the sleeve, therein providing a means for driving the sleeve downward (as more fully described hereinbelow with respect to the full assembly of the device, and with respect to FIG. 6).

With reference now to FIG. 6, which shows a side view of the fully locked coupling element 200, rod 250, and screw 120 system, the preferred method of implantation and assembly is described hereinbelow. First, a pre-drilled hole is provided in the bone, into which it is desired that the screw 120 be disposed. The hole may be pre-tapped, or the external threading 128 of the screw 120 may include a self-tapping lead edge. In either event, the head 122 of the screw 120 is inserted into the interior chamber 216 of the coupling element 200. At this point in the assembly process, the locking ring 230 has not yet been forced downward along the outwardly tapered lower portion 202 (as oriented in FIG. 3) thereby providing the screw 120 and the coupling element 200 with the capacity to rotate relative to one another.

By orienting the coupling element 200 and the screw 120 coaxially, the central bore 228 may be aligned with the recess 130 in the head 122 of the screw 120 so that a screw-driving tool may be used to drive the screw into the preformed hole in the bone.

Subsequent to the screw 120 being driven into the hole, the coupling element 200 may be rotated relative to the screw 120, to an angle such that support rod 250 may be properly nested within the rod receiving locus 222. After the rod 250 is appropriately positioned, the rod securing sleeve 240 is dropped over the element, such that the rod extends outward through the diametrically opposed vertical slots in the sleeve 240. At this stage of the assembly, the head 122 and the coupling element 200 remain rotationally free, and the locking ring 230 remains positioned at the top 212 of the lower portion 202 of the element. The rod securing sleeve 240 is prevented from fully descending onto the coupling element 200 as the bottom edge 248 thereof contacts, and is prevented from moving fully downward by the top surface 232 of the locking ring 230.

Once the proper angulation of the coupling element to the screw 120, and the secure nesting of the rod 250 within the receiving locus 222, have been established, the top locking nut 235 is threaded onto the upper portion 206 of the coupling element 200. As the nut descends, the lower surface 238 of the nut 235 seats against the top surface 242 of the rod securing sleeve 240 and the rod securing sleeve 240 is driven downward. This motion causes the locking ring 230 to be forced downward as well, relative to the lower portion 202 of the coupling element 200, therein causing the locking ring 230 to provide an inwardly directed deflecting force which causes the slots 220 in the lower portion 202 of the element to narrow. This deflection inward causes the inner surface 218 of the interior chamber 216 to crush lock against the head 122 of the screw 120. This clamping force locks the angulation of the screw 120 to the coupling element 200. In addition, the downward force of the nut 235 against the rod securing sleeve 240 further causes the uppermost curve 252 of the vertical slot of the sleeve 240 to lock the rod 250. This locking prevents the rod 250 from sliding relative to the assembled structure (along an axis which is perpendicular to the plane of FIG. 6). The full insertion of the top locking nut 235, therefore, locks the rod 250 to the coupling element 200, as well as the screw 120 to the coupling element 200.

Figure 7:
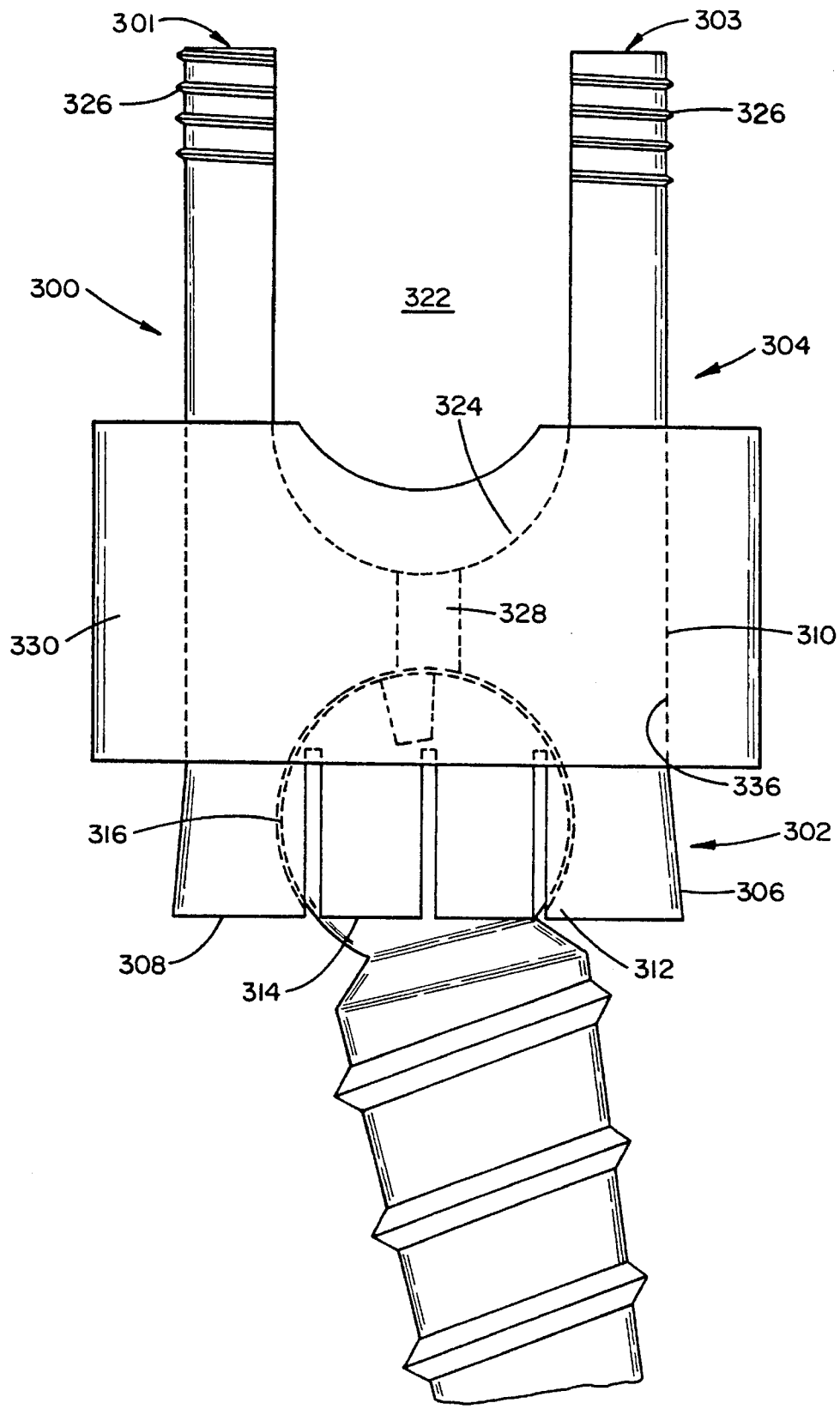
FIG. 7 is a side view of a second embodiment of the present invention wherein a coupling element similar to the one shown in FIG. 2 has the screw shown in FIG. 1 inserted into the interior chamber therein, and including a locking ring having grooves in the top edge thereof is shown in an unsecured position.

Referring now to FIG. 7, a second embodiment of the coupling element 300 of the present invention is shown in a side view, having a screw 120 such as is set forth more particularly with respect to FIG. 1 is inserted into its interior chamber 316, and having a locking ring 330 disposed about its lower portion. The coupling element itself is substantially similar to the coupling element 200 of the first embodiment, but for the upwardly extending members 301, 303, which define therebetween the rod receiving locus 322, which members 301, 303 do not extend so high as in the first embodiment. As above, the coupling element 300 comprises a generally cylindrical body having upper and lower portions 302, 304. The exterior surface 306 of the lower portion 302 includes a tapered portion 306, such that the bottom 308 is wider than the top 310 of the lower portion 302. The bottom 308 of the element includes an opening 314, defined by annular lip 312, which forms the mouth of an interior chamber 316. The lower portion 302 further includes a series of slots 320 which extend vertically upward from the bottom 308 in order that the application of an external deflecting force may widen or narrow the opening 314.

The upper portion 304 of the generally cylindrical body of the coupling element 300 includes a large removed section which forms a vertical channel which forms a rod receiving locus 322 in the top of the coupling element 300. The channel 322 comprises a curvate bottom 324. The top of the upper portion 304 of the coupling element 300 comprises a threading 326 which is ideally suited for receiving a top locking nut (see FIG. 4).

A central bore 328 extends from the bottom 324 of the rod receiving locus 322 into the interior chamber 316 of the coupling element 300. The bore 328 provides a linear passage through which a user may insert a screw-driving tool to access the interior chamber 316, and the recess 130 of the screw when the head 122 is disposed therein.

In FIG. 7, the coupling element 330 is shown in its pre-locked position about the top 310 of the lower portion 302. As above, with respect to the first embodiment, the locking ring 330 comprises a contiguous annular element having an inner diameter which is equal to or slightly larger than the outer diameter of the top 310 of the lower portion 302. In its initial and unlocked position, the top 332 of the locking ring 330 extends upwards, to a position above the bottom 324 of the rod receiving locus 322, and includes a pair of opposing curvate grooves 334 on which to receive the rod. Unlike the function of the first embodiment, it is the downward translation of the rod, as is set forth hereinbelow with reference to FIG. 8, which causes the locking collar 330 to descend and secure the screw 120 to the coupling element 300. Correspondingly, a rod securing sleeve is not necessary inasmuch as the top locking nut contacts the top of the rod and provides therethrough the force to downwardly translate the locking ring 330.

It is further understood that it is preferable for the interior surface 336 of the locking ring 300 to include a lower outwardly tapered portion 338 so that the downward translation of the ring 300 relative to the lower portion 302 is not hindered by any binding mechanisms associated with the moving of a sharp angled edge through a distance to engage a friction lock.

Figure 8:
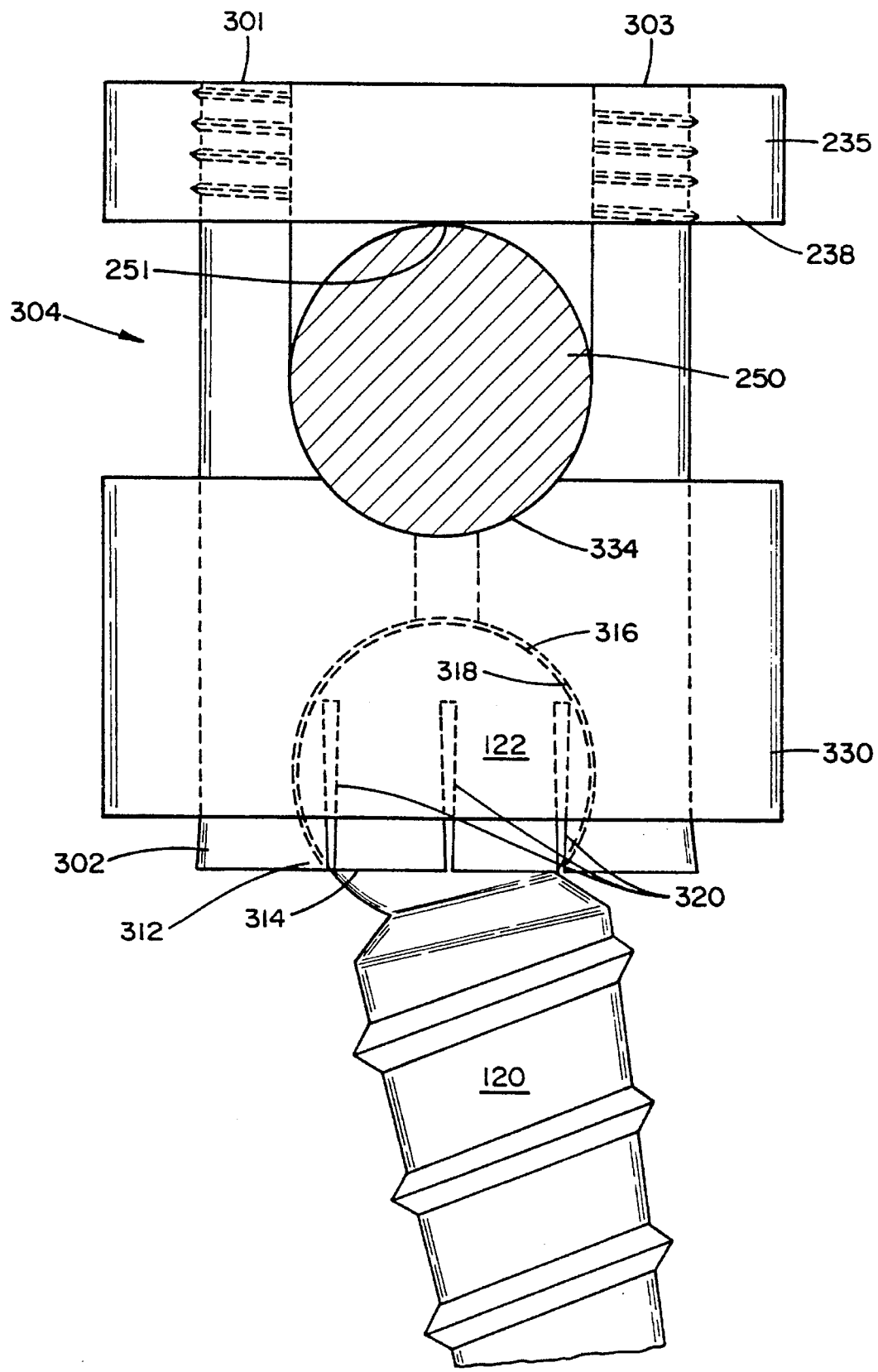
FIG. 8 is a side cross-sectional view of the second embodiment of the present invention in its fully assembled disposition having a rod securely locked therein.

With reference now to FIG. 8, which shows a side view of the fully locked coupling element 300, rod 250, and screw 120 system, the preferred method of implantation and assembly is described hereinbelow. First, a pre-drilled hole is provided in the bone, into which it is desired that the screw 120 be disposed. The hole may be pre-tapped, or the external threading 128 of the screw 120 may include a self-tapping lead edge. In either event, the head 122 of the screw 120 is inserted into the interior chamber 316 of the coupling element 300. The screw 120 and the coupling element 300 have the capacity to rotate relative to one another.

By orienting the coupling element 300 and the screw 120 coaxially, the central bore 328 may be aligned with the recess 130 in the head 122 of the screw 120 so that a screw-driving tool may be used to drive the screw into the preformed hole in the bone.

Subsequent to the screw 120 being driven into the hole, the coupling element 300 may be rotated relative to the screw 120, to an angle such that support rod 250 may be properly nested within the rod receiving locus 322, and disposed on the grooves 334 of the locking collar 300. Once the proper angulation of the coupling element 300 to the screw 120, and the secure nesting of the rod 250 on the pair of grooves 334, have been established, the top locking nut 235 is threaded onto the threading of the upwardly extending members 301, 303 of the coupling element 300. The lower surface 238 of the nut 235 seats against the top surface 251 of the rod. As the nut 235 rotates, and descends relative to the coupling element 300, the rod 250 is driven downward therein forcing the locking ring 330 to descend as well. By descending along the tapered lower portion 302 of the element, the locking ring 330 provides an inwardly directed deflecting force which causes the slots 320 in the lower portion 302 of the element to narrow so that the collar may proceed downward. This deflection inward causes the inner surface 318 of the interior chamber 316 to crush lock against the head 122 of the screw 120. This clamping force locks the angulation of the screw 120 to the coupling element 300.

In addition, the downward force of the nut 235 against the rod 250 and the upward resistance of the locking ring 330, once fully descended into position, causes the rod 250 to be locked between the grooves 304 and the bottom surface 238. This locking prevents the rod 250 from sliding relative to the assembled structure (along an axis which is perpendicular to the plane of FIG. 8).

Figure 9:
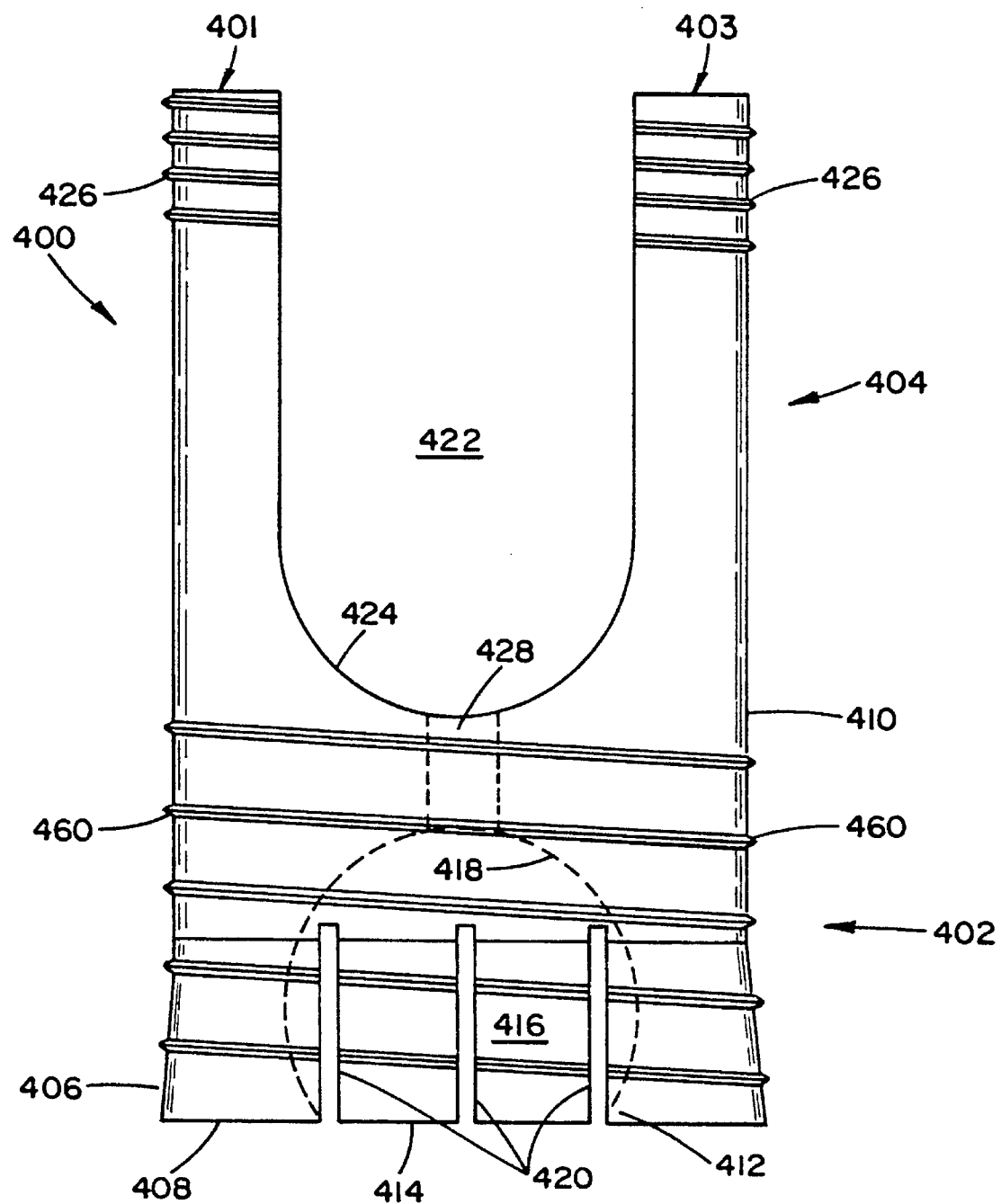
FIG. 9 is a side view of the coupling element of a third embodiment of the present invention.

Referring now to FIG. 9, a coupling element 400 of the third embodiment of the present invention, having a threaded lower portion 402 is shown in a side view. In this embodiment the locking ring (see FIG. 10) may be independently translated downward to lock the angulation of the screw to the coupling element, without regard to a rod securing sleeve, or the downward translation of the top locking nut which may be placed over the rod and coupling element subsequently. More specifically, with respect to the coupling element 400 itself, which is otherwise similar to the coupling elements of the first and second embodiments, the lower portion 402 comprises an exterior surface 406 which is tapered in the elongate direction such that the body is wider at the bottom 408 than at the top 410 thereof. The bottom 408 of the element includes an opening 414, defined by annular lip 412, which forms the mouth of an interior chamber 416. As is the case with the first embodiment, the diameter of the opening 414, when otherwise unaffected by external deflecting forces, is more narrow than the maximum diameter of the interior chamber 416. The interior chamber 416 has a generally curvate inner surface which is correspondingly shaped to receive the semi-spherical head 122 of the screw 120.

The exterior surface 406 of the lower portion 402 includes a threading 460 and a series of slots 420 which extend vertically upward from the bottom 408 of the element to a position above the widest point of the interior chamber 416. The slots 420 are provided in order that the application of an external deflecting force may widen or narrow the opening 414.

The upper portion 404 of the generally cylindrical body of the coupling element 400 is equivalent to those portions 204 of the first embodiment. The upper portion 404 includes a large vertical channel, which comprises a rod receiving locus 422, having a curvate bottom surface 424. The depth of the channel 422 is established such that a circular support rod (see FIG. 12) may be fully nested within the rod receiving locus 422 and is therein substantially lower than the top of the upwardly extending members 401, 403, between which the channel 422 is disposed. This ensures the proper insertion of the rod securing sleeve (such as shall be described with reference to FIGS. 11 and 12), so that it may slide over the element 400 to retain the rod within the rod receiving locus 422.

The top of the upper portion 406, which comprises the top of the upwardly extending members 401, 403, includes a threading 426 thereon which is ideally suited for receiving top locking nut 235. In addition, as is the case with the first embodiment, a central bore 428 extends from the bottom surface 424 of the rod receiving channel 422 to the interior chamber 416. The bore 428 provides a linear passage through which a user may insert a screw-driving tool to access the interior chamber 416, and the screw head 120 therein.

Figure 10:
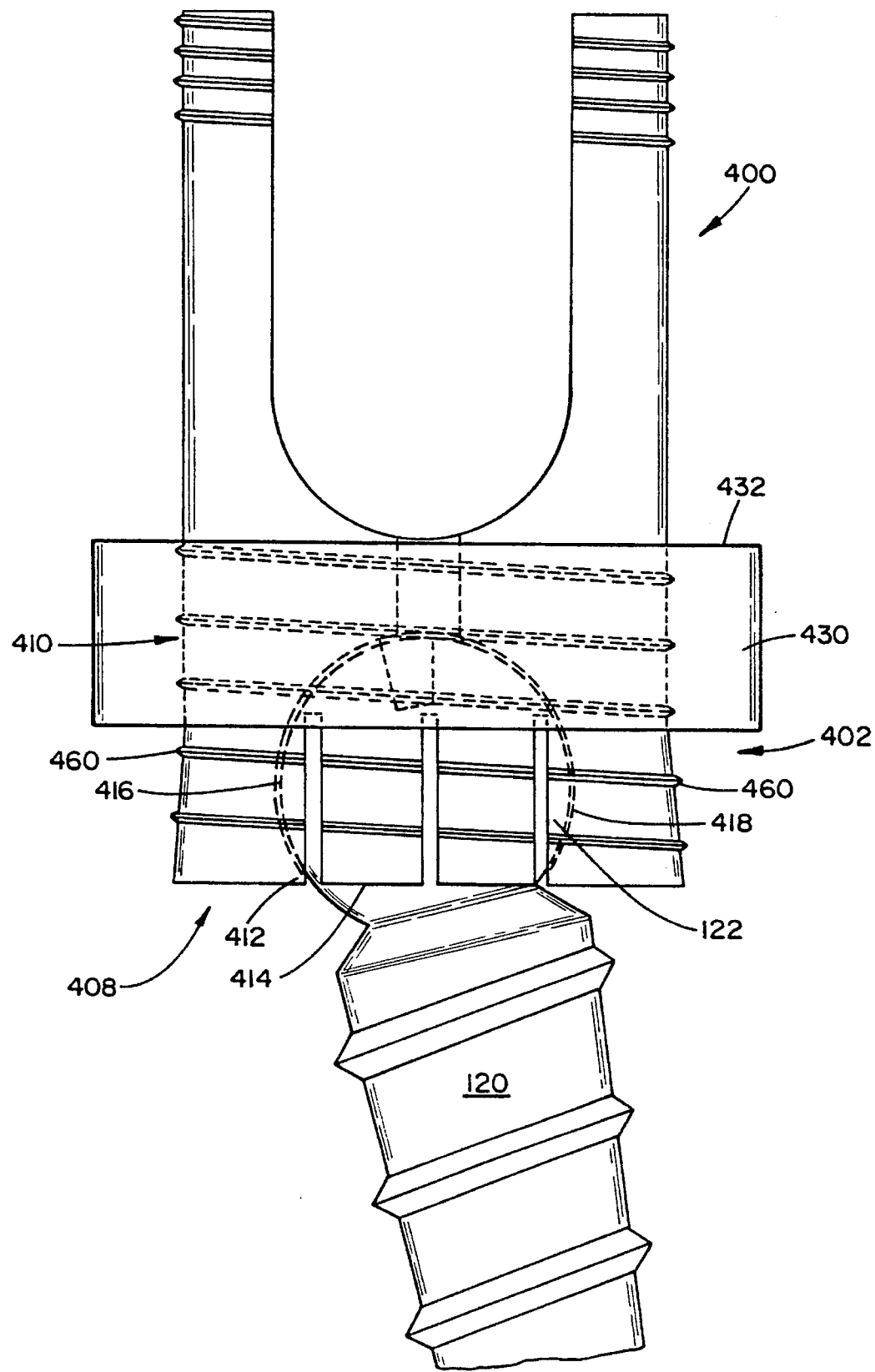
FIG. 10 is a side view of the coupling element shown in FIG. 9, having the screw shown in FIG. 1 inserted into the interior chamber therein, and including a threaded locking ring in an unsecured position.

Referring now to FIG. 10, the coupling element 400, as described more fully with respect to FIG. 9, is shown in a side view, wherein the head 122 of the screw 120 has been received within the interior chamber 416, and a threaded locking ring 430 is shown in its pre-locked position about the top 410 of the lower portion 402. The head 122 of the screw 120 is rotationally free to move relative to the coupling element, within the interior chamber 416, however, it is prevented from fully separating from the coupling element by the annular lip 412 at the bottom 408 of the lower portion 402. The locking ring 430 comprises a contiguous annular element having an inner diameter which is equal to the outer diameter of the lower portion 402 at the top 410 thereof, and a corresponding threading on the inner surface thereof. In order to lock the screw 120 into an angle relative to the coupling element 400, therein eliminating the freedom of the screw 120 to swing relative to the element, the locking ring 430 may be rotated so that it translates downward along the threading 460 of the lower portion 402. The threading 460 of the lower portion 402 may include an upper slide prevention means, for example a thickened thread (not shown) so that the ring 430 cannot move upward, thereby preventing separation of the locking ring 430 during handling prior to use. In the alternative, a dowel or protuberance may be provided to serve the equivalent function. The top surface 432 of the locking ring 430 is designed to mate easily with the rod securing sleeve (see FIG. 11).

Figure 11:
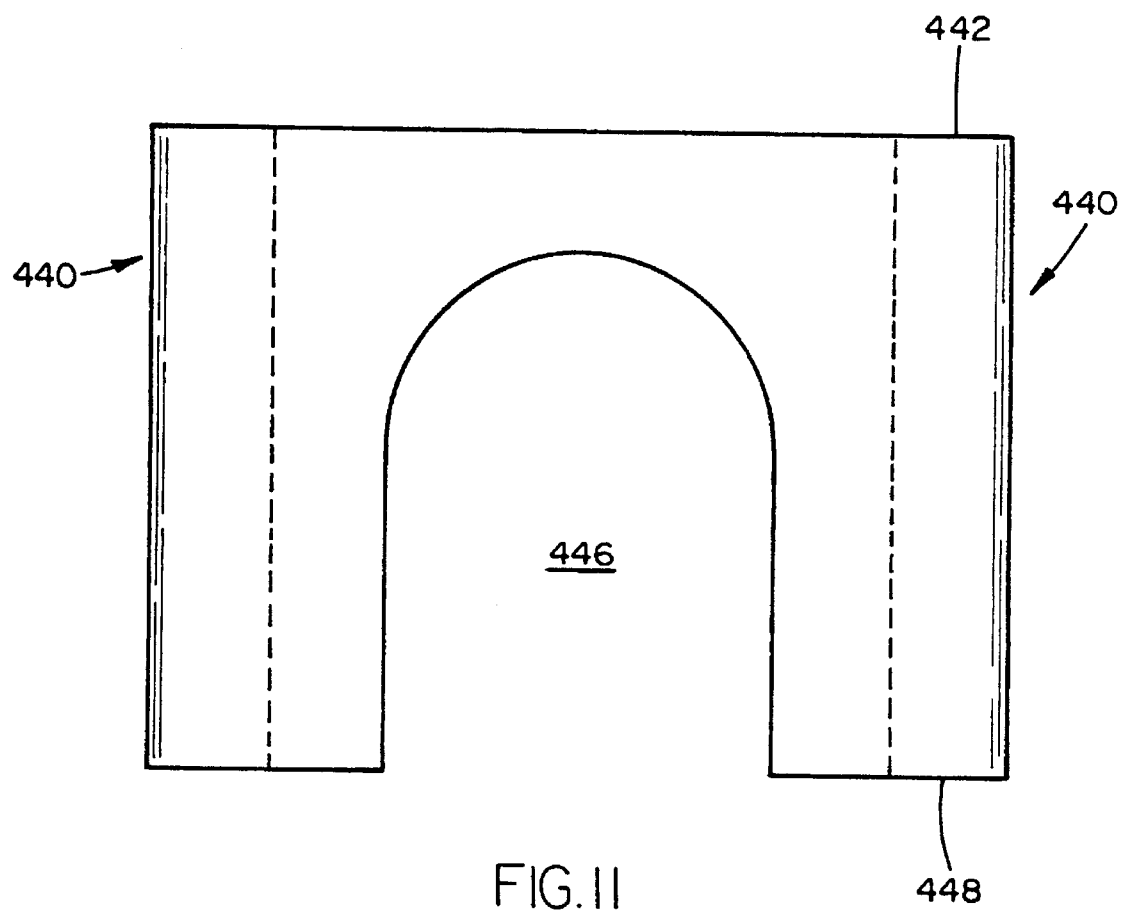
FIG. 11 is a side view of the rod securing sleeve of the third embodiment, shown along a direction wherein the vertical slots thereof are aligned perpendicular to the plane of view.

Referring now to FIG. 11, a rod securing sleeve 440 of the third embodiment is shown in side cross-section views. Similar to the sleeve 240 of the first embodiment, rod securing sleeve 440 comprises a hollow cylindrical body 444 having diametrically opposing vertical slots 446, which together define a passage through the sleeve 400 for the positioning of a rod therethrough. The interior diameter of the sleeve 440 is equal to the outer diameter of the coupling element, so that it may be placed thereover. The vertical slots 446 correspond to the channel or rod receiving locus 422 such that the support rod which is inserted therein (see FIG. 12) may pass therethrough. The bottom edge 448 of the rod receiving sleeve 440 of the second embodiment may be designed to fit securely with the upper surface 432 of the locking ring 430, or it may simple seat against it for the purposes of preventing it from backing up the threads 460 of the coupling element 400.

Figure 12:
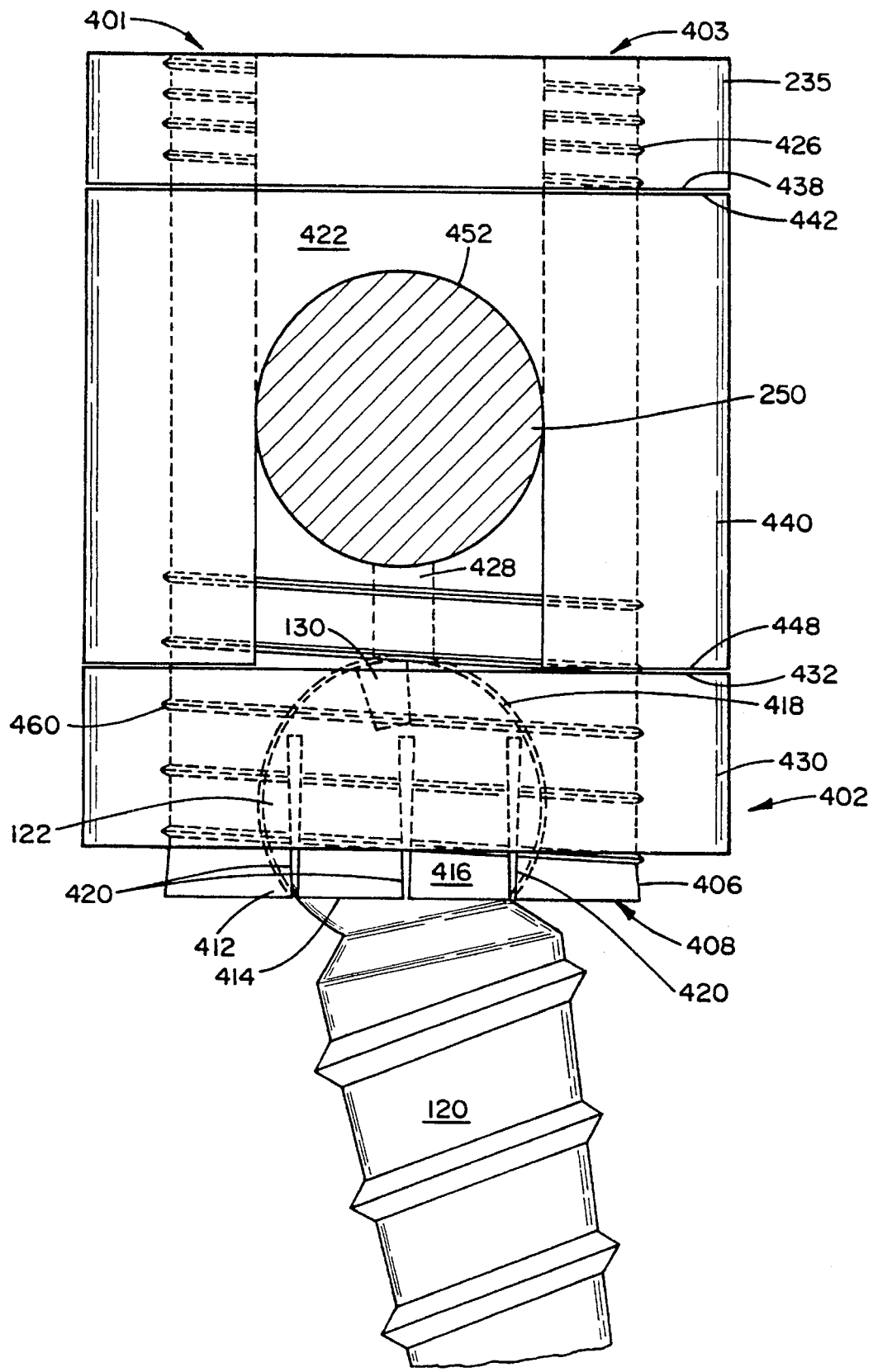
FIG. 12 is a side cross-sectional view of the third embodiment of the present invention in its fully assembled disposition having a rod securely locked therein.

With reference now to FIG. 12, which shows a side view of the fully locked coupling element 400, rod 250, and screw 120 assembly, the preferred method of implantation and assembly is described hereinbelow. As described with respect to the implantation of the first and second embodiments, prior to its insertion into the bone, the head 122 of the screw 120 is positioned in the interior chamber 416 of the coupling element 400. A hole is then drilled into the bone, into which the screw 120 is inserted. The coupling element 400 and the screw 120 are rotated relative to one another so that the screw-driving tool may access the recess 130 in the head 122 for easy implantation. Once the screw 120 has been fully inserted, however, the coupling element 400 is moved relative to the screw 120 into the ideal orientation for receiving the rod 250. At this point, the threaded locking ring 330 is rotated downward to lock the screw 120 to the coupling element by forcing the vertical slots 420 in the lower portion 402 together, therein crush locking the interior surface 418 to the external surface of the head 122.

Subsequent to the locking of the screw 120 to the coupling element 400 the support rod 250 is positioned within the rod receiving locus 422. Once the rod 250 is properly nested, the rod securing sleeve 440 is dropped over the assembly such that the rod extends outward through the diametrically opposed vertical slots 446 in the sleeve 440. Unlike in the case of the first embodiment, the rod securing sleeve 440 may fully descend onto the coupling element 400 without being prevented from doing so by virtue of the locking ring's 430 presence.

In order to fully lock the rod 250 to the coupling element 400, and to lock the rod securing sleeve 440 in position, the top locking nut 235 is threaded onto the upper portion 404 of the coupling element 400. The lower surface 238 of the nut 235 seats against the top surface 442 of the rod securing sleeve 440 preventing it from translating upward. In addition, the nut 235 causes the uppermost curve 452 of the vertical slot 446 of the sleeve 440 to crush lock to the rod 250. This locking prevents the rod 250 from sliding relative to the assembled structure (along an axis which is perpendicular to the plane of FIG. 12). The downward force of the descending top locking nut 235, therefore, locks the rod 250 to the coupling element 400, and the threaded locking ring locks the screw 120 to the coupling element 400. It is preferable that the bottom surface 448 of the rod securing sleeve 440 seat against the upper surface 432 of the locking ring 430, to prevent the ring 430 from translating back up the lower portion. It is understood, however, that unlike the first embodiment, the locking of the screw 120 to the coupling element 400 by the locking ring 430 may be entirely separate and independent from the locking of the sleeve 440 and rod 250 to the coupling element 400 by the top locking nut 235. It is understood that the threading 460, along which the locking ring 430 is rotated, and the threading 426 along which the top locking nut 235 is rotated may be oppositely oriented so as to prevent sympathetic loosening in vivo.

While there has been described and illustrated several embodiments of a polyaxial screw and coupling element assembly for use with posterior spinal rod implantation apparatus, it will be apparent to those skilled in the art that variations and modifications are possible without deviating from the broad spirit and principle of the present invention. The present invention shall, therefore, be limited solely by the scope of the claims appended hereto.

We claim:

1. A polyaxial screw and coupling element assembly for use with orthopedic rod implantation apparatus, comprising:

a screw having a curvate head;

a coupling element including
an expandable and contractable interior chamber for receiving therein said curvate head,
a rod receiving locus for receiving therein a rod, and
a surface threading disposed on an upper exterior portion thereof;

a locking ring mounted around said coupling element, the downward translation of said ring providing a force which causes said interior chamber to contract, therein locking the screw to the coupling element; and a top locking nut, mateable with said surface threading.

2. The coupling assembly as set forth in claim 1, wherein said currate head is semi-spherical.

3. The coupling assembly as set forth in claim 1, wherein said coupling element further comprises at least one vertical slot extending upward from an opening, therein rendering said interior chamber expandable and contractable.

4. The coupling assembly as set forth in claim 3, wherein a portion of said coupling element which contains said interior chamber comprises a downwardly widening taper, whereby the downward translation of said locking ring causes the interior chamber to contract.

5. The coupling element as set forth in claim 4, wherein said coupling element comprises a second threading disposed about an outer surface thereof, at least a portion of which includes the at least one vertical slot, and wherein said locking ring includes a threading on an interior surface thereof, mateable with said second threading, wherein said locking ring may be downwardly translated on said second threading, thereby locking said screw to said coupling element.

6. The coupling element as set forth in claim 4, wherein said locking ring comprises a pair of grooves on an upper edge thereof for receiving thereon said rod, wherein the downward translation of said nut on said threading causes the rod to translate downward, and for the rod to cause the locking ring to translate downward thereby locking the screw to said coupling element, and locking said rod between said grooves of said locking ring and a lower surface of said nut.

7. The coupling assembly as set forth in claim 1, further comprising a rod securing sleeve, mounted about said coupling element for securely retaining said rod within said rod receiving locus.

8. The coupling assembly as set forth in claim 7, wherein a bottom surface of said top locking nut seats against a top surface of said rod securing sleeve, wherein the downward translation of said top locking nut causes said rod securing sleeve to crush lock said rod to said coupling element.

9. The coupling assembly as set forth in claim 8, wherein a bottom surface of said rod securing sleeve seats against a top surface of said locking ring, wherein the downward translation of said nut on said exterior threading of said coupling element causes the downward translation of said locking ring to crush lock the screw within said interior chamber.

10. The coupling element as set forth in claim 7, wherein said coupling element comprises a second threading disposed about an outer surface thereof, at least a portion of which includes the at least one vertical slot, and wherein said locking ring includes a threading on an interior surface thereof, mateable with said second threading, wherein said locking ring may be downwardly translated on said second threading, thereby locking said screw to said coupling element.

11. A polyaxial screw and coupling element assembly for use with orthopedic rod implantation apparatus, comprising:

a screw having a semi-spherical head;

a coupling element including
a downwardly widening tapered lower portion having an expandable and contractable interior chamber and an expandable and contractable opening at a mouth thereof, for receiving therein and therethrough said semi-spherical head, and at least one vertical slot in the exterior thereof extending upward from said opening, therein rendering said interior chamber and said opening expandable and contractable, a rod receiving locus for receiving therein a rod, and a surface threading disposed on an upper exterior portion thereof;

a locking ring mounted around said coupling element, the downward translation of said ring providing a force which causes said interior chamber to contract, therein locking the screw to the coupling element; and a top locking nut, mateable with said surface threading.

12. The coupling assembly as set forth in claim 11, further comprising a rod securing sleeve, mounted about said coupling element for securely retaining said rod within said rod receiving locus.

13. The coupling assembly as set forth in claim 12, wherein a bottom surface of said top locking nut seats against a top surface of said rod securing sleeve, wherein the downward translation of said top locking nut causes said rod securing sleeve to crush lock said rod to said coupling element.

14. The coupling assembly as set forth in claim 13, wherein a bottom surface of said rod securing sleeve seats against a top surface of said locking ring, wherein the downward translation of said nut on said exterior threading of said coupling element causes the downward translation of said locking ring to crush lock the screw within said interior chamber.

15. The coupling element as set forth in claim 14, wherein said coupling element comprises a second threading disposed about an outer surface thereof, at least a portion of which includes the at least one vertical slot, and wherein said locking ring includes a threading on an interior surface thereof, mateable with said second threading, wherein said locking ring may be downwardly translated on said second threading, thereby locking said screw to said coupling element.

16. The coupling element as set forth in claim 11, wherein said coupling element comprises a second threading disposed about an outer surface thereof, at least a portion of which includes the at least one vertical slot, and wherein said locking ring includes a threading on an interior surface thereof, mateable with said second threading, wherein said locking ring may be downwardly translated on said second threading, thereby locking said screw to said coupling element.

17. The coupling element as set forth in claim 11, wherein said locking ring comprises a pair of grooves on an upper edge thereof for receiving thereon said rod, wherein the downward translation of said nut on said threading causes the rod to translate downward, and for the rod to cause the locking ring to translate downward thereby locking the screw to said coupling element, and locking said rod between said grooves of said locking ring and a lower surface of said nut.

18. An orthopedic rod implantation apparatus, comprising:

at least one elongate rod;

at least one screw having a curvate head;

at least one coupling element including an expandable and contractable interior chamber for receiving therein said curvate head.

a rod receiving locus for receiving therein one of said at least one elongate rod, and a surface threading disposed on an upper exterior portion thereof;

a locking ring mounted around each of said at least one coupling element, the downward translation of said ring providing a force which causes said interior chamber to contract, therein locking the screw to the coupling element; and a top locking nut, mateable with said surface threading of said at least one coupling element.

19. The apparatus as set forth in claim 18, wherein said curvate head is semi-spherical.

20. The apparatus as set forth in claim 18, wherein said at least one coupling element further comprises at least one vertical slot extending upward a bottom thereof, therein rendering said interior chamber expandable and contractable.

21. The apparatus as set forth in claim 20, wherein a portion of said coupling element which contains said interior chamber comprises an exterior surface taper, said portion being wider at said opening, whereby the downward translation of said locking ring causes the interior chamber and said opening to contract.

22. The coupling assembly as set forth in claim 21, wherein a portion of said at least one coupling element which contains said interior chamber comprises a downwardly widening taper, whereby the downward translation of said locking ring causes the interior chamber to contract.

23. The coupling element as set forth in claim 22, wherein at least one of said at least one coupling element comprises a second threading disposed about an outer surface thereof, at least a portion of which includes the at least one vertical slot, and wherein said locking ring includes a threading on an interior surface thereof, mateable with said second threading, wherein said locking ring may be downwardly translated on said second threading, thereby locking said screw to said coupling element.

24. The coupling element as set forth in claim 21, wherein said locking ring comprises a pair of grooves on an upper edge thereof for receiving thereon said rod, wherein the downward translation of said nut on said threading causes the rod to translate downward, and for the rod to cause the locking ring to translate downward thereby locking the screw to said coupling element, and locking said rod between said grooves of said locking ring and a lower surface of said nut.

25. The coupling assembly as set forth in claim 18, further comprising a rod securing sleeve, mounted about each of said at least one coupling element for securely retaining said rod within said rod receiving locus.

26. The coupling assembly as set forth in claim 25, wherein a bottom surface of said top locking nut seats against a top surface of said rod securing sleeve, wherein the downward translation of said top locking nut causes said rod securing sleeve to crush lock said rod to said coupling element.

27. The coupling assembly as set forth in claim 26, wherein a bottom surface of said rod securing sleeve seats against a top surface of said locking ring, wherein the downward translation of said nut on said exterior threading of said coupling element causes the downward translation of said locking ring to crush lock the screw within said interior chamber.

28. The coupling element as set forth in claim 25, wherein at least one of said at least one coupling element comprises a second threading disposed about an outer surface thereof, at least a portion of which includes the at least one vertical slot, and wherein said locking ring includes a threading on an interior surface thereof, mateable with said second threading, wherein said locking ring may be downwardly translated on said second threading, thereby locking said screw to said coupling element.

\* \* \* \* \*